(12) United States Patent
Ten Kate et al.

(10) Patent No.: US 11,911,148 B2
(45) Date of Patent: Feb. 27, 2024

(54) MONITORING A SUBJECT

(71) Applicant: KONINKLIJKE PHILIPS N.V., Eindhoven (NL)

(72) Inventors: Warner Rudolph Theophile Ten Kate, Waalre (NL); Doortje Van De Wouw, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 323 days.

(21) Appl. No.: 17/285,812

(22) PCT Filed: Oct. 16, 2019

(86) PCT No.: PCT/EP2019/078069
§ 371 (c)(1),
(2) Date: Apr. 15, 2021

(87) PCT Pub. No.: WO2020/079071
PCT Pub. Date: Apr. 23, 2020

(65) Prior Publication Data
US 2021/0378550 A1  Dec. 9, 2021

Related U.S. Application Data

(60) Provisional application No. 62/746,582, filed on Oct. 17, 2018.

(51) Int. Cl.
*A61B 5/11* (2006.01)
*G16H 20/30* (2018.01)
(Continued)

(52) U.S. Cl.
CPC .......... *A61B 5/1114* (2013.01); *A61B 5/6824* (2013.01); *A61H 3/04* (2013.01); *G16H 20/30* (2018.01); *G16H 40/63* (2018.01)

(58) Field of Classification Search
CPC ..... A61B 5/1118; A61B 5/0004; A61B 5/681; A61B 2562/0219; A61B 5/1114;
(Continued)

(56) References Cited

U.S. PATENT DOCUMENTS 7,111,121 B2 *  9/2006  Oishi .................. G06F 21/6218
                                                              711/115
2015/0206409 A1    7/2015  Visvanathan et al.
(Continued)

FOREIGN PATENT DOCUMENTS

KR      2017025252 A    3/2017
WO      2015063765 A1   5/2015
(Continued)

OTHER PUBLICATIONS

Vermeiren, D. et al., "Detecting Human Motion: Introducing Step, Fall and ADL Algorithms", Institute for Computer Sciences, Social-Informatics and Telecommunications Engineering 2010.
(Continued)

*Primary Examiner* — Eric F Winakur
*Assistant Examiner* — Elina Sohyun Ahn

(57) ABSTRACT

Presented are concepts for monitoring walker usage by a subject. One such concept obtains movement data comprising values of detected movement of an arm of the subject for a first time period during which the subject is determined to have transferred between first and second locations the first time period. It is determined if the subject used a walker during the first time period based on a measure of variance in the values of detected movement of the subject's arm during the first time period.

14 Claims, 6 Drawing Sheets

(51) Int. Cl.
*G16H 40/63* (2018.01)
*A61B 5/00* (2006.01)
*A61H 3/04* (2006.01)

(58) Field of Classification Search
CPC ... A61B 5/6824; A61B 5/1123; A61B 5/6831; A61B 5/0002; A61B 5/0024; A61B 5/1112; A61B 5/1117; A61B 5/4833; G01C 22/006; A61H 2201/5084; A61H 3/04; A61H 2003/006; A61H 2201/1635; A61H 2003/046; A61H 2003/043; A61H 3/061; A61H 3/02; A61H 2201/165; A61H 2201/0173; G01P 15/00; G01P 13/00; G06F 1/163; G08B 25/016; G08B 21/0446; A47D 13/04; B60L 2200/24; A61G 5/047; A61G 5/08; A61G 5/066
See application file for complete search history.

(56) References Cited

U.S. PATENT DOCUMENTS

2016/0220153 A1    8/2016  Annegarn et al.
2018/0344217 A1*  12/2018  Perry .................. A61B 5/0004

FOREIGN PATENT DOCUMENTS

| WO | 2015113915 A1 | 8/2015 |
| WO | 2016061668 A1 | 4/2016 |
| WO | 2016168463 A1 | 10/2016 |

OTHER PUBLICATIONS

Pirsiavash, H. et al., "Detecting Activities of Daily Living in First-person Camera Views", 2012 IEEE.
International Search Report and Written Opinion, International Application No. PCT/EP2019/078069, dated Jan. 22, 2020.
Po-Chan, Y. et al., "Using walker during walking: a pilot study for health elder", Work 41, 2012.

* cited by examiner

MONITORING A SUBJECT

CROSS-REFERENCE TO PRIOR APPLICATIONS

This application is the U.S. National Phase application under 35 U.S.C. § 371 of International Application No. PCT/EP2019/078069, filed on 16 Oct. 2019, which claims the benefit of U.S. Provisional Patent Application No. 62/746,582, filed on 17 Oct. 2018 These applications are hereby incorporated by reference herein.

FIELD OF THE INVENTION

This invention relates generally to monitoring a subject, such as a person or patient, and more particularly to monitoring walker usage by a subject.

BACKGROUND OF THE INVENTION

Aging people experience a decline in their physical abilities. At some point, it may become advisable (e.g. for safety and well-being) for an aging or disabled person to use a walker (sometimes otherwise referred to as a walking frame), which is a tool for disabled or elderly people who need additional support to maintain balance or stability while walking.

In general, people will find the usage of a walker a relief, but sometimes they may choose not to use the walker and to transfer between locations without it.

A carer, care assistant, medical assistant or family member concerned about a user of a walker may want to learn about, and/or monitor, the walker usage by the user. Beyond simply asking the user, an objective measure of walker usage may be helpful in monitoring and/or coaching the user of a walker.

A straight-forward approach to monitoring walker usage is to instrument the walker with a corresponding motion sensor. However, the drawback of this approach is that a dedicated sensing device and system needs to be acquired and installed, leading to additional burden and costs.

SUMMARY OF THE INVENTION

The embodiments described herein aim to at least partly fulfil the aforementioned needs. To this end, the described embodiments provide systems and methods as defined in the independent claims. The dependent claims provide advantageous embodiments.

There is provided a system for monitoring walker usage by a subject, the system comprising: an input interface adapted to obtain an indication of a first time period during which the subject is determined to have transferred between first and second locations; a data acquisition unit adapted to obtain movement data comprising values of detected movement of an arm of the subject during the first time period; a data analysis unit adapted to determine a measure of variance in the values of detected movement of an arm of the subject during the first time period; and a monitor unit adapted to determine if the subject used a walker during the first time period based on the determined measure of variance.

Proposed is a concept for determining if a subject has used a walker based on detected arm movement. By analysing the variation of detected movement of a subject's arm for a window of time that the subject has been identified as walking, it may be inferred whether or not the subject used a walker. For example, by assessing deviations (e.g. variations) in movement detected by an arm-worn movement sensor, embodiments may determine if a walker was used. Embodiments may therefore facilitate monitoring of walker usage. This may help evaluation purposes, for example to assess if a subject shows a pattern in walker usage and/or a reluctance to use a walker.

For example, embodiments employ a principle of identifying a time period when a subject transfers between two locations (e.g. walks between two rooms) and then observing, for the identified time period, data from a movement sensor worn on an arm of the subject (such as on an upper arm, elbow, forearm, wrist or hand of the subject). Such a time period may be identified by a user (e.g. carer or family member) and then indicated via user interface. Alternatively, or additionally, a time period may be identified using a monitoring system that is adapted to detect when a subject transfers between two locations and provide a signal indicating the time period.

It is proposed that, in the case that the subject used a walker for the identified time period, a signal representing detected movements over time should be smooth and of low variance. Conversely, it is proposed that, in the case that the subject did not use a walker for the identified time period, a signal representing detected movements over time will be bumpy/rough and of high variance.

A subject's user of a walker may therefore be inferred using movement data from a single arm-worn movement sensor (e.g. accelerometer), and the subject may already be equipped with such a sensor (e.g. for activity/health monitoring and/or fall-detection purposes). Proposed embodiments may therefore infer information about a subject's walker usage from the existing sensing devices/infrastructure in a simple, cheap and non-obtrusive manner. This may help to reduce associated cost and/or complexity of a monitoring system. For instance, embodiments may avoid the need for new or additional sensors (and complex signal processing of their respective signals) and may instead simply employ existing monitoring/sensing arrangements.

Embodiments may be based on a proposal to determine walker usage based on variations in detected arm movement during a time period that a subject travels between locations. Improved (e.g. more accurate or more convenient) monitoring of a subject's walker usage, and thus health or well-being) may therefore be facilitated by using information obtained by proposed embodiments.

Embodiments may be of particular relevance to patient monitoring since, for example, it may assist in the detection of walker usage patterns for a subject. Proposed concepts may also facilitate signalling improvement or deterioration in the health status of a monitored subject.

In some proposed embodiments, the monitor unit may be adapted: to compare the determined measure of variance with a threshold value; and to determine the subject has not used a walker during the first time period if the determined measure of variance exceeds the threshold value. Simple mathematical functions may therefore be employed, enabling straight-forward and reduced-complexity implementation.

In some embodiments, the monitor unit is adapted to determine the threshold value based on at least one of: a user input provided to the system; a predetermined value; and the subject.

Further, the monitor unit may be adapted to determine the threshold value based on a value of a physiological property of the subject, and preferably the physiological property may comprise height, weight, age, gender or level of fitness.

This may provide the advantage that specific attributes of the subject can be used to more accurately determine walker usage based on detected variations in arm movement during the identified first time period. This may provide the advantage that more accurate determinations/assessments may be made. It may also cater for unique characteristics or properties associated with the monitored subject.

The input interface may be adapted to receive a signal comprising an indication of the first time period. By way of example, the signal may be generated by a monitoring system that is adapted to detect when the subject moves between locations.

In some embodiments, the input interface may comprise a user input interface (such as a GUI and/or physical input devices like a touchscreen or keyboard and mouse) that is adapted to receive a user input identifying the first time period. In this way, a user (such as a care giver or family member) may provide an indication of time period (e.g. containing a subject ID and parameter describing the time period (such as begin & end or; begin & duration)).

Embodiments may be further adapted to receive a user input for defining or modifying a threshold value and/or physiological data.

The data analysis unit may be adapted to determine a measure of variance in the values of detected movement of the subject's arm during the first time period based on at least one of: an average value of the values of detected movement; a median value of the values of detected movement; maximum and minimum values of the values of detected movement; a median of absolute deviations from the median value of the values of detected movement; a value of standard deviation of the values of detected movement. Simple mathematical functions may therefore be employed, enabling straight-forward and reduced-complexity implementation.

In other embodiments, the data analysis unit may be adapted to obtain a frequency domain representation of the values of detected movement of the subject's arm during the first time period, and to determine a measure of variance in the values of detected movement of the subject's arm during the first time period based on at least one of: a mean or median frequency of the frequency domain representation of the values of detected movement; a comparison of low and high frequency bands of the frequency domain representation of the values of detected movement; and a modal frequency of the frequency domain representation of the values of detected movement. Various different approaches to determining a measure of variance may therefore be employed, and these may each provide different advantages or benefits depending on implementation specifics.

Embodiments may further comprise a sensor arrangement adapted to detect movement of the subject between the first and second locations and to generate an indication of the first time period during which the subject is detected to have transferred between first and second location. Preferably, the sensor arrangement may comprise at least one of: an accelerometer; a gyroscope; a movement sensor; a weight sensor; a pressure sensor; a passive infra-red sensor; and a wireless communication signal strength sensor. Further, the sensor may be adapted to be coupled to the subject or the object.

For example, there exist many sensors that can be employed by a system according to an embodiment. Typical sensors include PIR (Passive Infra-Red; measure movement and presence), OC (open-close; measure state of doors, in particular front doors, windows, and cupboards, including refrigerators), and pressure sensors or mats (measure occupancy of user sitting in chair, lying in bed, standing on door mat in front of front door, being at toilet, etc.). Many others exist and are conceivable, such as sensors to signal light switch state, etc. A further range of sensors are those based on physical quantities, such as accelerometers, magnetometers, gyroscopes, and air pressure sensors. Accelerometers, for example, can also be used to measure speed or velocity of movement of a subject or an object moved by the subject. Displacement can also be estimated, in particular over small distances during short time intervals. Yet another range of sensors consists of microphones and cameras (including infra-red, or even UV and beyond, part of spectrum), to which also belong GPS and location-sensitive IR. Ultrasound or RF-based sensors, including RFID tagging, provide additional input. Appliances having an own IP-address, known as the internet-of-things, provide further sensor input signals that can be taken by the smart-home system.

Although the sensor arrangement may comprise one or more sensors mounted in a monitoring environment (e.g. the subject's home), they may also be attached to user utilities (such as a keyring) or put in clothes, in a pocket or bag, or as insole or undergarment, etc. They may also be fabricated to be worn explicitly like a wrist watch or pendant. By way of further example, some embodiments may employ a sensor arrangement that is adapted to be coupled to (or carried by) the subject.

Further, the sensor arrangement may communicate output signals to an interface of an embodiment via a wired or wireless connection, or a combination thereof.

The sensor arrangement may be positioned in a strategic position so that it detects the appropriate value(s) without the subject needing to intentionally or consciously activate/operate the sensor arrangement. In this way, a monitored subject may only need to undertake their normal activities. Such strategic positioning may ensure that movement of the subject between two locations can be automatically and accurately detected, and this may not require the subject to remember to undertake any special or additional activities in order for a value to be detected by the sensor. This may remove the risk of the subject forgetting to activate a sensor (e.g. by pressing a button), for example.

Non-intrusive monitoring may therefore be realized with relatively simple sensors that provide data on specific properties of the subject (such as movement, weight, speed, weight, and/or distance travelled for example). Such sensors for sensing activity of the subject may be simple, small and/or cheap.

Thus, a sensor arrangement of various embodiments may employ conventional sensors and/or existing sensor arrangements. Also, embodiments may employ sensors that are considered to be non-intrusive and more easily accepted by the monitored subject. Yet, with the data provided by these sensors, the reliability or usefulness of variations in a subject's vital signs may be determined and provide information on the subject being monitored.

Such sensors may be employed by, or in conjunction with, embodiments so as to increase the number and/or accuracy of detected activity or movement. They may also be used to confirm or qualify readings taken by a primary sensor, so that spurious or unintentional measurements are avoided. For example, signals from a location sensor worn by the monitored subject may be used to confirm if movement readings taken by a movement sensing system are indeed attributable to the monitored subject.

Some embodiments may include the movement sensor that is adapted to be worn on an arm of the subject and to generate movement data comprising values of detected movement of the subject's arm. It may be preferable to adapt the movement sensor to be worn on a forearm, wrist or hand of the subject.

Put another way, an arm-worn movement sensor may be provided as part of the proposed system (e.g. where an appropriate movement sensor is not already available). Such an arm-worn movement sensor that is provided as part of an embodiment may, however, also be useful for other monitoring purposes (such as fall detection for example). Thus, unlike conventional approaches which employ a dedicated sensor attached to a walker (which therefore has no other purpose), proposed embodiments have the advantages that an arm-worn movement sensor may be useful for other monitoring purposes as well.

However, to avoid needing to provide an additional device to the monitored subject, proposed embodiments may be designed to work with existing/conventional arm-worn movement sensing devices that are already worn by monitored subjects, such as PERS and fall-detection sensors or activity/health watches/trackers. Such embodiments may therefore be advantageous because they do not require the use of additional, dedicated movement sensing devices.

Embodiments may therefore be implemented in conjunction with pre-existing, pre-installed or otherwise separately-provisioned movement sensors that are adapted to be worn on the arm of a monitored subject, and the output signals from such sensors may be received and processed in accordance with proposed concepts.

A sensor employed by an embodiment may be adapted to undertake primary processing of the detected values, such a signal filtering, sampling, conditioning, etc., so as to reduce required transmission bandwidth and/or transmission duration for example. Alternatively, a sensor may send raw data.

Embodiments may be further adapted to store data in a database adapted to store historical data relating to one or more previously determinations of walker usage. Previously obtained data and/or determined values may therefore be stored, in a historical database for example, and then used in subsequent calculations. Furthermore, currently determined values may be used to re-calculate or refine a previously determined trend pattern, prediction or estimation of walker usage.

It will be appreciated that all or part of a proposed system may comprise one or more data processing units. For example, the system may be implemented using a single processor which is adapted to undertake data processing in order to determine walker usage of a monitored subject.

A system for monitoring walker usage by a subject may be remotely located from the subject, and a signal representative of detected movement of the subject may be communicated to the system unit via a communication link.

The system may comprise: a server device comprising the input interface, data acquisition unit, data analysis unit and monitor unit; and a client device comprising the arm-worn sensor. Dedicated data processing means may therefore be employed for the purpose of monitoring walker usage by a subject, thus reducing processing requirements or capabilities of other components or devices of the system.

The system may further comprise a client device, wherein the client device comprises the input interface, data acquisition unit, data analysis unit and monitor unit and a display system. In other words, a user (such as a care giver) may have an appropriately arranged client device (such as a laptop, tablet computer, mobile phone, PDA, etc.) which processes received data in order to determine if a subject used a walker during an identified time period.

Thus, processing may be hosted at a different location from where the movement sensing happens. For example, for reasons of power efficiency (e.g. to improve battery lifetime) it might be advantageous to execute only part of the processing at the sensor location, thereby reducing associated costs, processing power, transmission requirements, etc.

Thus, it will be understood that processing capabilities may therefore be distributed throughout the system in different ways according to predetermined constraints and/or availability of processing resources.

Embodiments may also enable some of the processing load to be distributed throughout the system. For example, pre-processing may be undertaken at an arm-worn movement sensor. Alternatively, or additionally, processing could be undertaken at a communication gateway. In some embodiments, processing may be undertaken at a remote gateway or sever, thus relinquishing processing requirements from an end-user or output device. Such distribution of processing and/or hardware may allow for improved maintenance abilities (e.g. by centralising complex or expensive hardware in a preferred location). It may also enable computational load and/or traffic to be designed or located within a networked system according to the processing capabilities available. A preferable approach may be to process movement sensor signals locally and transmit extracted data for full processing at a remote server.

The reliability unit may be further adapted to generate an output signal based on the determined walker usage of the subject. Embodiments may be adapted to provide an output signal to at least one of: the subject; a medical practitioner; and a caregiver. The output signal may thus be provided to a user or monitoring system for the purpose of monitoring walker usage for example.

The monitor unit may be further adapted to generate a control signal for modifying a graphical element based on the determined walker usage. Further, the system may further comprise a display system adapted to display the graphical element in accordance with the control signal generated by the monitor unit. In this way, a user (such as a care giver) may have an appropriately arranged display system that can receive and display information about walker usage of the monitored subject, and that user may be remotely located from the subject. Embodiments may therefore enable a user to remotely monitor a subject (e.g. patient) using a portable display device, such as a laptop, tablet computer, mobile phone, PDA, etc.

According to various embodiments, there is provided a method for monitoring walker usage by a subject, the method comprising: obtaining an indication of a first time period during which the subject is determined to have transferred between first and second locations; obtaining movement data comprising values of detected movement of an arm of the subject during the first time period; determining a measure of variance in the values of detected movement of an arm of the subject during the first time period; and determining if the subject used a walker during the first time period based on the determined measure of variance.

According to various embodiments there is provided computer program product for monitoring walker usage by a subject, wherein the computer program product comprises a computer-readable storage medium having computer-readable program code embodied therewith, the computer-readable program code configured to perform all of the steps of an embodiment.

A computer system may be provided which comprises: a computer program product according to an embodiment; and one or more processors adapted to perform a method according to an embodiment by execution of the computer-readable program code of said computer program product.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Figure 1:
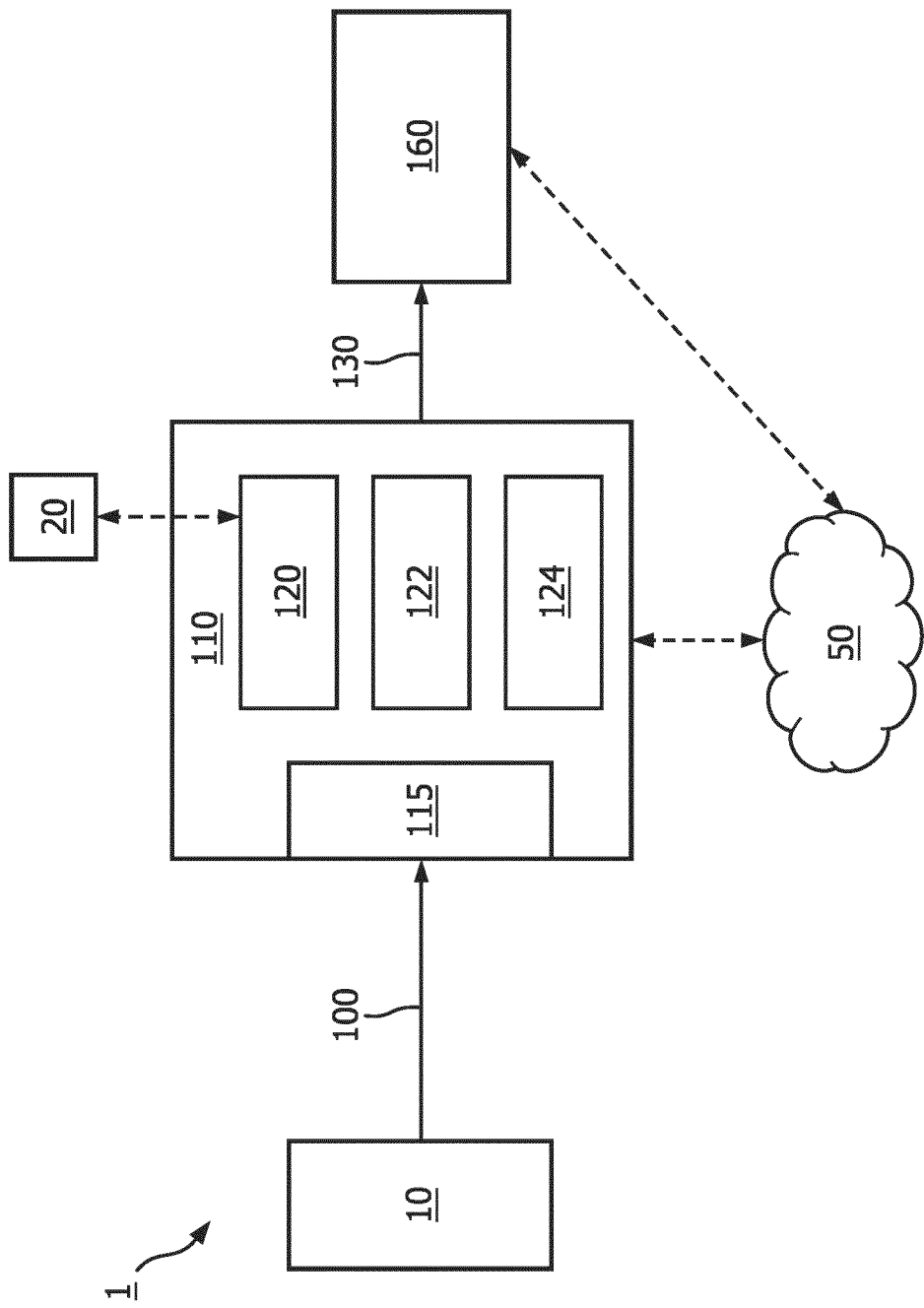
FIG. 1 is a simplified block diagram of a system for monitoring a subject according to an embodiment.

Proposed is a concept for identifying walker usage of a subject, which may be useful for improving health deterioration assessment and monitoring for example. Such subjects may, for instance, include a disabled person, an elderly person, a rehabilitation patient, an injured person, a medical patient, etc. Elderly persons can mean persons above 50 years, above 65 years, above 70, or above 80 years old, for example.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments may be implemented.

Embodiments are directed toward enabling an objective measure of walker usage to be obtained. Such information may therefore be useful for improved monitoring convenience or efficiency, e.g. by avoiding a need for a care giver to visually monitor a subject and/or provide a subjective assessment of walker usage.

Embodiments employ the concept of determining if a subject has used a walker during an identified time period based on movement data for the identified period, the movement data being from a movement sensor worn on an arm of the subject. In particular, it is proposed that a measure of variance in the values of detected movement of the subject's arm for the identified time period can be analysed to determine if the subject used a walker during the identified time period. For example, if the variance in the values of detected movement of the subject's arm during the identified time period is low (e.g. variations in the detected values of movement are smooth and of low variance), it can be inferred that the subject used a walker during the identified time period.

By determining walker usage, embodiments may enable the provision of an objective measure of walker usage. This may help to provide more accurate and convenient monitoring. Thus, embodiments may be useful for evaluation or monitoring purposes, for example to assess if a subject shows a significant improvement (or deterioration) in a physical health.

Movement of the subject between locations (e.g. passage between rooms) may be detected or inferred from sensor output signals and there already exist systems and methods for such detection or inference of a time period during which the subject transfers between first and second locations. Accordingly, the proposed concepts may be used in conjunction with existing presence, activity or movement detection or monitoring systems/methods.

Also, movement of a subject's arm or wrist may be detected or inferred from movement sensor output signals and there already exist systems and methods for such detection or inference of movement of a subject.

For example, Dries Vermeiren et al describe a system based on 2 tri-axial accelerometers to detect the Activities of Daily Living (ADLs) of a patient in a paper entitled "Detecting Human Motion: Introducing Step, Fall and ADL algorithms". Also, H Pirsiavas et al describe algorithms for detecting ADLs in first-person camera views in paper entitled "Detecting activities of daily living in first-person camera views" (CVPR, 2012). Because many such ADL detection or monitoring methods/systems are known and any one or more of these may be employed, detailed description of such methods/systems is omitted from this description.

FIG. 1 shows an embodiment of a system 1 comprising a sensor arrangement 10 adapted to detect movement of the subject between the first and second locations and to generate an indication of the first time period during which the subject is detected to have transferred between first and second locations.

Here, the sensor arrangement 10 comprises conventional Activity of Daily Living (ADL) monitoring system that is adapted to detect the presence of a subject in various regions/areas (e.g. rooms) of a monitored environment (e.g. residential building or care home). The ADL monitoring system may thus comprise various open-close (OC) and Passive Inra-Red (PIR) sensors situated throughout the monitored environment. Alternatively, or additionally, the ADL monitoring system may comprise: an accelerometer; a gyroscope; a movement sensor; a weight sensor; a pressure sensor; and a wireless communication signal strength sensor.

Of course, many more sensors may be employed so as to provide signals indicative of detected values of properties of activity of the subject. Such additional signals may also be used to confirm or qualify values detected by the sensor arrangement 10, so that spurious or unintentional measurements are avoided. For example, signals from a location sensor worn or carried by the monitored subject may be used to confirm if values detected by the sensor arrangement 10 are indeed attributable to the monitored subject walking between two locations, for example.

The system 1 also comprises an arm-worn movement sensor 20 that is worn by the monitored subject. Here, the movement sensor 20 is integrated into a watch, bracelet or Personal Emergency Response System (PERS) device that is worn by the monitored subject so that it moves with movement of the subject's arm. For example, the movement sensor 20 may comprise an accelerometer, magnetometer, and gyroscope.

Accordingly, a subject need only to undertake their normal activities when being monitored and may not even be aware that they are operating the sensor arrangement 10 and the movement sensor 20 and thus being monitored. Such configuration of sensor arrangement 10 and the movement sensor 20 may enable walking and movement of the subject to be detected without requiring the subject to remember to undertake any special or additional activities in order for a movement or activity of the subject to be detected. For example, it can remove the need for a subject to perform a specific additional action (e.g. pressing a button) in order to activate the movement sensor 20.

The sensor arrangement 10 is adapted to determine when the subject moves between first and second locations (e.g. by walking). The sensor arrangement 10 is further adapted to output sensor output signals 100 which are representative of a first time period during which the subject is determined to have transferred (e.g. walked between first and second locations.

The sensor arrangement 10 communicates its output signals 100 via a wired or wireless connection. By way of example, the wireless connection may comprise a short-to-medium-range communication link. For the avoidance of doubt, short-to-medium-range communication link may be taken to mean a short-range or medium-range communication link having a range of up to around one hundred (100) meters. In short-range communication links designed for very short communication distances, signals typically travel from a few centimetres to several meters, whereas, in medium-range communication links designed for short to medium communication distances, signals typically travel up to one hundred (100) meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave. Here, the output signals are not encrypted for communication via the wired or wireless connection in a secured manner. However, it will be appreciated that, in other embodiments, one or more encryption techniques and/or one or more secure communication links may be employed for the communication of signals in the system.

The system further comprises a data processing system 110 for monitoring walker usage by a subject. The system 110 has an input interface 115 adapted to receive the sensor output signals 100. In this way, the input interface 115 is adapted to receive an indication of a first time period during which the subject is determined to have transferred between first and second locations.

The data processing system 110 also comprises a data acquisition unit 120 adapted to obtain movement data from the arm-worn movement sensor 20 that is worn by the monitored subject. Here, the data acquisition unit 120 retrieves movement data from arm-worn movement sensor 20 so that obtained movement data comprises (at least) values of detected movement of the subject's arm during the first time period.

The obtained movement data is provided to a data analysis unit 122 of the data processing system 110. The data analysis 122 unit is adapted to process the obtained movement data to determine a measure of variance in the values of detected movement of the subject's arm during the first time period. For this purpose, the data analysis 122 of the system 110 may communicate with one or more data processing resources available in the Internet or "cloud" 50. Such data processing resources may undertake part or all of the processing required to determine a measure of variance.

Thus, it will be appreciated that the embodiment may employ distributed processing principles.

In this example, the data analysis unit 122 is adapted to determine a measure of variance in the values of detected movement of the subject's arm during the first time period based on at least one of: the standard deviation in the movement sensors's signal, an average value of the values of detected movement; a median value of the values of detected movement; maximum and minimum values of the values of detected movement; a median of absolute deviations from the median value of the values of detected movement; a value of standard deviation of the values of detected movement. Such measures can be computed per axis monitored by movement sensor (3D) accelerometer and subsequently taken together to arrive at a single (scalar) number. Alternatively, the signals from multiple axes (e.g. X, Y and Z can be combined first and the variance over that combined signal then computed. For example, the norm of an accelerometer signal from the movement sensor computed. The variance can be computed over the whole range of the requested time period. It can also be computed over subsequent or overlapping segments in the time period, for example segments of one second duration.

The determined measure of variance is provided to a monitor unit 124 of the data processing system 110. The monitor unit 124 adapted to analyse the determined measure of variance to determine if the subject used a walker during the first time period. Again, for this purpose, the monitor unit 124 may communicate with one or more data processing resources available in the Internet or "cloud" 50. Such data processing resources may undertake part or all of the processing required to determine if the subject used a walker during the first time period based on the determined measure of variance.

In this example, the monitor unit 124 is adapted to compare the determined measure of variance with a threshold value, and to then determine the subject has not used a walker during the first time period if the determined measure of variance exceeds the threshold value. For this purpose, the monitor unit 124 may determines threshold value based on at least one of: a user input provided to the system; a predetermined value; and the subject. In particular, in this embodiment, the monitor unit 124 is adapted to determine the threshold value based on a value of a physiological property of the subject, such as height, weight, age, gender or level of fitness for example. This enables the monitor unit 124 to cater for specific attributes of the monitored subject and thus provide for a more accurate assessment of the determined measure of variance.

The data processing system 110 is further adapted to generate an output signal 130 representative of a determined walker usage of the monitored subject. In other words, after determining if the subject used a walker during the first time period, an output signal 130 representative of or determined walker usage is generated.

The system further comprises a graphical user interface (GUI) 160 for providing information to one or more users. The output signal 130 is provided to the GUI 160 via wired or wireless connection. By way of example, the wireless connection may comprise a short-to-medium-range communication link. As indicated in FIG. 1, the output signal 130 is provided to the GUI 160 from the data processing unit 110. However, where the system, has made use of data processing resources via the internet or cloud 50), an output signal may be made available to the GUI 160 via the internet or cloud 50.

Based on the output signal 130, the GUI 160 is adapted to communicate information by displaying one or more graphical elements in a display area of the GUI 160. In this way, the system may communicate information about determined walker usage that may be useful for indicating underlying changes in a subject's physical capability and/or pattern of walker usage. For example, the GUI 160 may be used to display graphical elements to a medical practitioner, a caregiver, a family member or close relative. Alternatively, or in addition, the GUI 160 may be adapted to display graphical elements to the monitored subject. Further, other forms of output interfaces may be employed to provide output signals indicative of determined walker usage, such as a haptic feedback or vibratory signal interface, an audio output interface (e.g. speaker), and/or a visual output interface (e.g. lights, LED array, etc.).

From the above description of the embodiments of FIG. 1, it will be understood that there may be proposed a system for identifying whether a monitored subject has used a walker during a time period that has been identified as being when then subject transferred between first and second locations. Such an exemplary system can be considered to comprise three main sub-systems/functions: (i) The first is an identification of a time period when the subject transfers (e.g. walks or travels) between two locations—this may, for example, comprise employing an existing or conventional ADL monitoring system that monitors an environment within which subject undertakes their normal activities. Alternatively, or additionally, it may employ an interface (such as a GUI or user input interface) adapted to obtain an indication of an identified time period from a user (such as a carer or family member); (ii) The second comprises acquiring values of detected movement of the subject's arm that occurred during the identified time period—this may comprise obtaining a signal representative of detected motion from a motion sensor positioned on (or coupled to) the subject's hand or arm; and (iii) The third implements an algorithm which determines if a walker was used by assessing the variance in the acquired values of detected movement of the subject's arm that occurred during the identified time period.

Such an approach has been found to be accurate and effective, because it has been identified that whenever a subject is walking without the aid of a walker (even when carrying a tray for example) there is exhibited an increased variance in the movement of the subject's arm.

Further, in some example, alternative or additional sub-systems/functions may be included, such as:

(ia): Identifying when the subject moves from one location to another. This movement may, for example, be walking (with or without walker), cycling, car, wheelchair etc.;

(ib) Determining if the person was walking. This may be achieved using a PERS device around the neck of the subject, or using a phone carried by the subject. This may eliminate other modes by which the movement from one location to another occurred.

By way of further example, identification of walking (as opposed to travelling by bike, car, etc.) may be based on a detected speed of the subject. By setting certain boundary conditions for walking, embodiment may eliminate movement via car and/or bicycle for example. Also, movement caused by being pushed in a wheelchair may be eliminated by using a sensor measuring the height of the wrist (as this is generally lower in a wheelchair compared to walking with a walker).

Figure 2A:
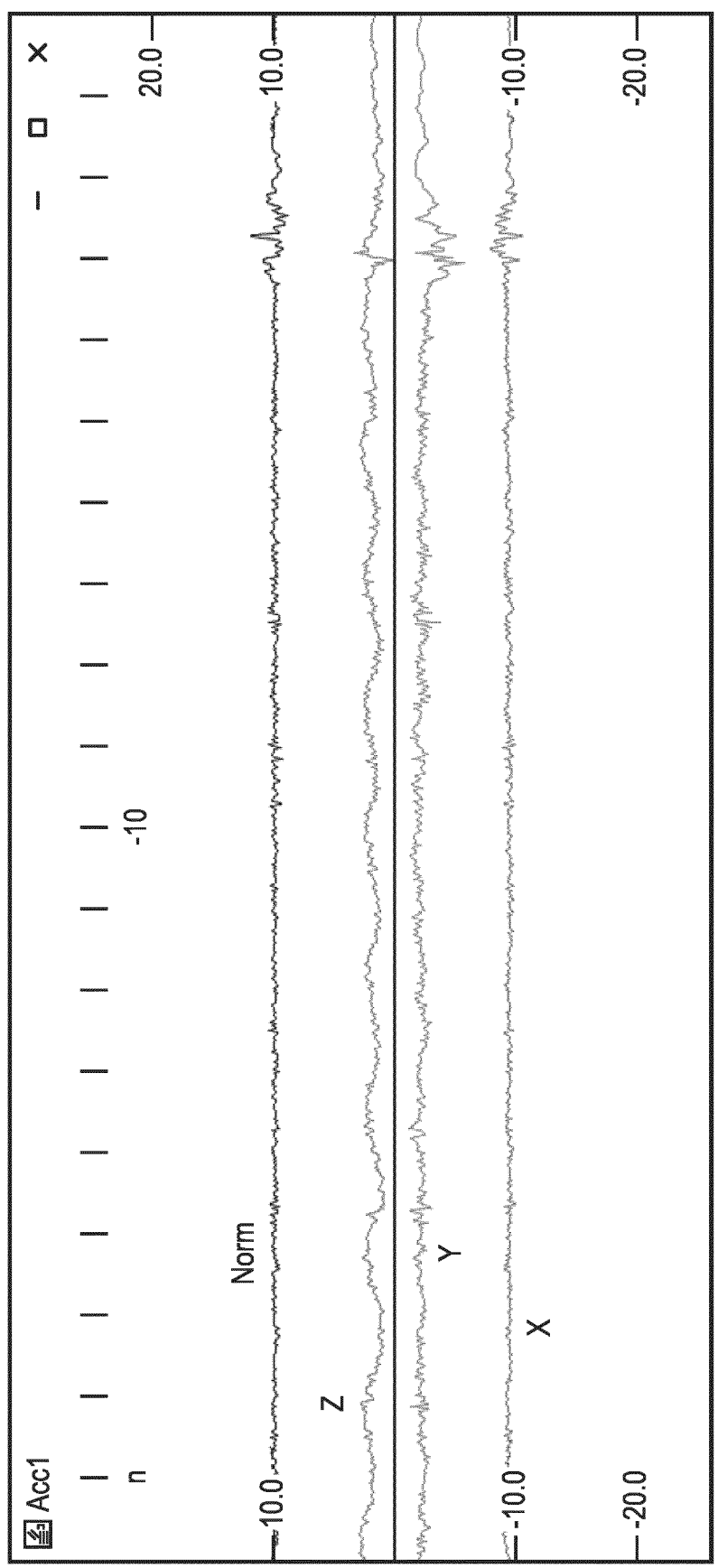
FIGS. 2A, 2B and 2C are exemplary plots of signals received from a wrist-worn sensor against time for three differing walking instances.
Figure 2B:
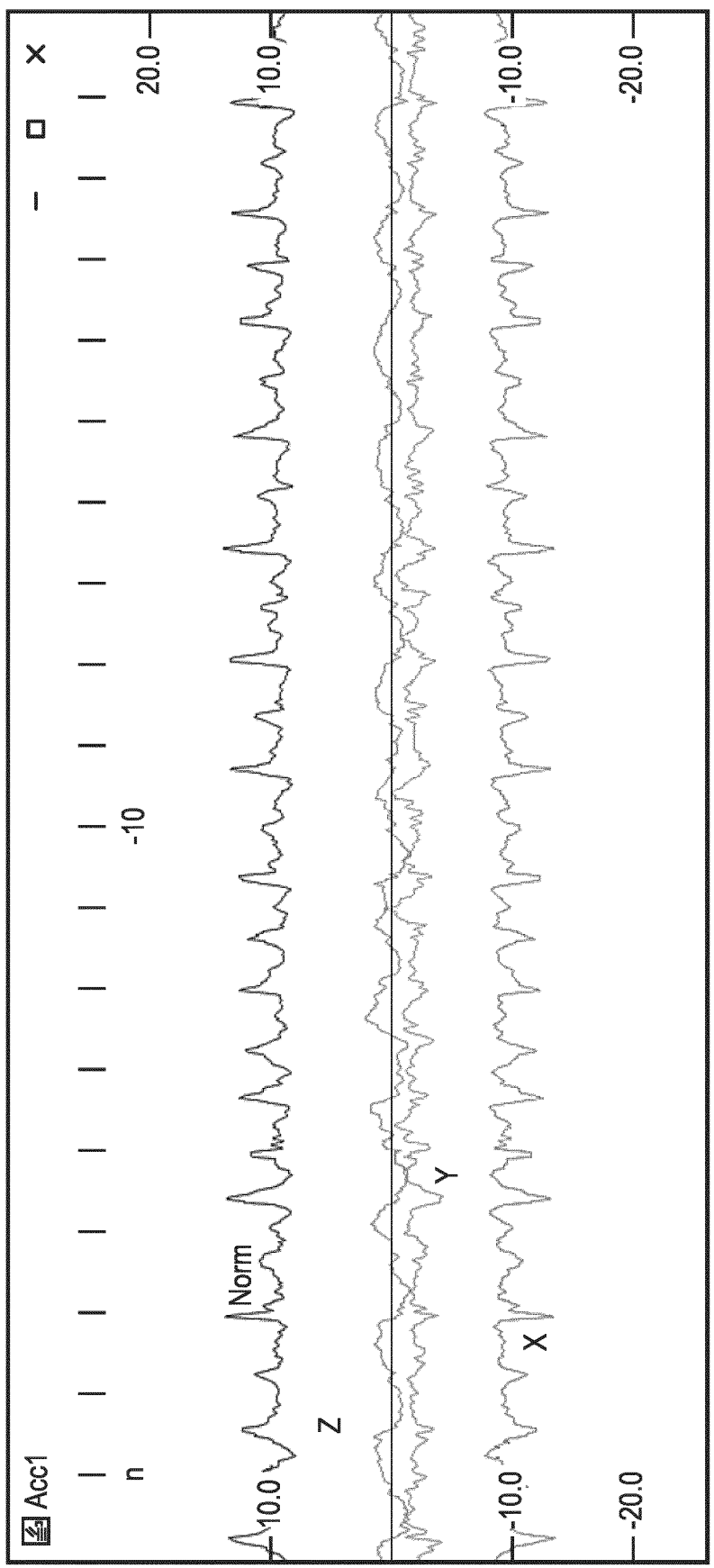
Figure 2C:
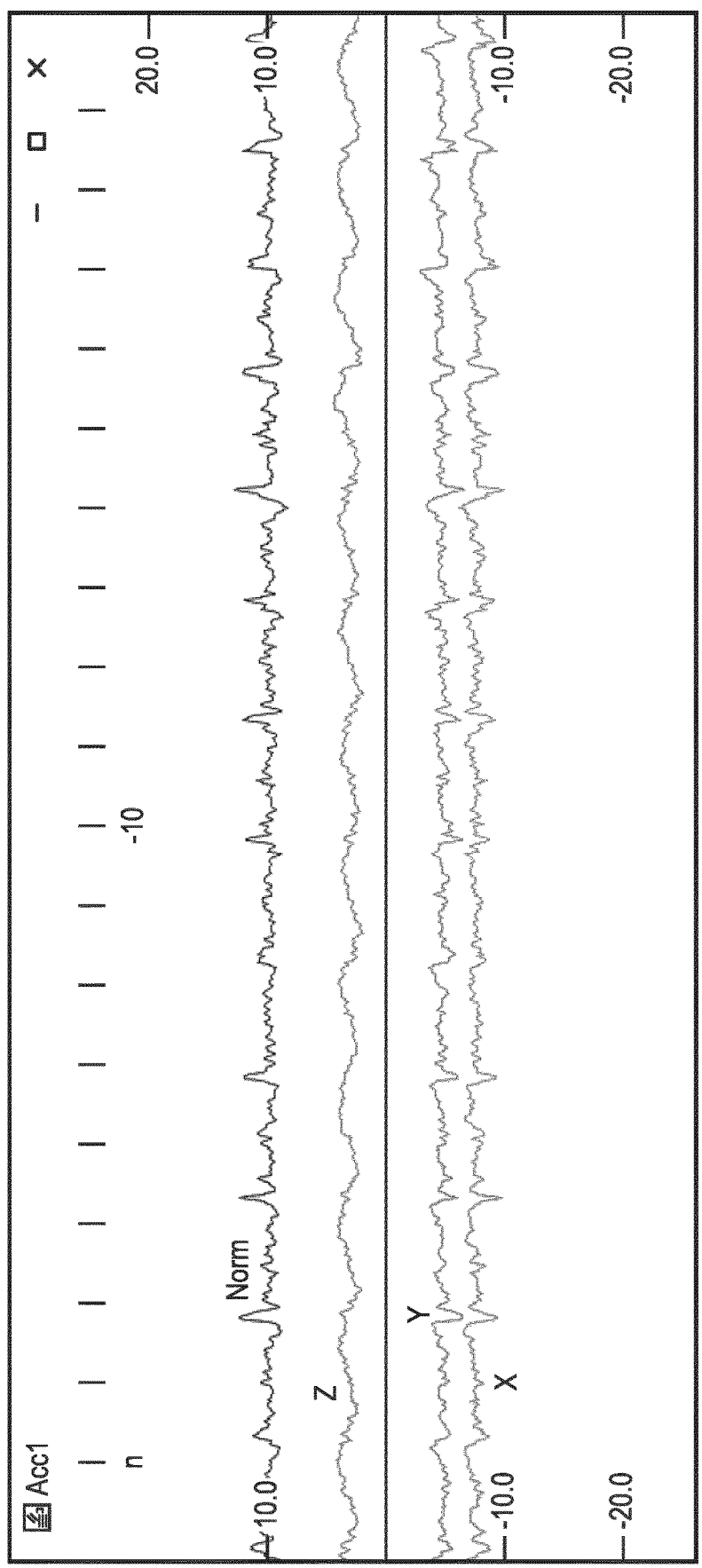

By way of example, referring now to FIGS. 2A-2C there are depicted plots of the signals received from a wrist-worn sensor against time for three differing situations. More specifically, FIG. 2A shows signals of detected X, Y, Z and Norm movements against time as received from a wrist-worn sensor as the subject walks with the aid of (i.e. uses) as walker. FIG. 2B shows signals of detected X, Y, Z and Norm movements against time as received from a wrist-worn sensor as the subject walks without the aid of (i.e. does not use) as walker. FIG. 2C shows signals of detected X, Y, Z and Norm movements against time as received from a wrist-worn sensor as the subject walks without the aid of (i.e. does not use) as walker while holding a tray.

It will be seen from a comparison of the individual signals between FIG. 2A and FIGS. 2B-2C, that the variance in the values of detected movement of the subject's wrist is significantly reduced when subject walks with the aid of (i.e. uses) as walker. Thus, a low measure of variance in the values of detected movement of the subject's wrist is indicative of walker usage. Conversely, a (relatively) high measure of variance in the values of detected movement of the subject's wrist is indicative of a walker not being used by the subject.

Although the above example demonstrates the differences in signals for a wrist-worn sensor, it will be understood that other embodiments may employ signals from a movement sensor worn on a different part of a subject-arm. For instance, although employing movement of a subject's wrist (e.g. using signals from a wrist-worn sensor) may be preferable, other embodiments may be adapted to determine walker usage based on a variance in the values of detected movement of the subject's hand, forearm, elbow or upper arm. Thus, values of detected movement from a movement sensor worn on a hand, forearm, elbow or upper arm (or upper limb) of a subject may be employed.

Various different approaches or method for measuring the smoothness and variance of the values of detected movement of the subject's arm (e.g. wrist-worn accelerometer signal(s)) may be employed. Purely by way of example, various methods may be summarised as follows:

An arm-worn accelerometer signal is first delimited by the identified period of observation (e.g. the first time period during which the subject is determined to have transferred between first and second locations). This period is then segmented in smaller parts, for time windows of thirty (30) seconds duration. Instead of segmenting the identified period of observation, a moving window could be defined. Each window (of the 30 seconds duration) overlaps with its neighbouring windows, e.g. for 10 or 15 seconds.

In each segment/window the variance of the accelerometer signal is computed. This can be on the norm of the signal, or per axis (e.g. X, Y and Y) separately (or a subset of axes). In the latter case, the three values are combined (taking average, median, max, etc.).

Alternative variance metrics include the MAD (Median of Absolute Deviations from the median), max-min distance, or other interquartile ranges. It is also noted that some de-trending may be applied first.

Another exemplary variance metric may be obtained by determining, for example, the max-min per small time period (e.g. 0.5-1.0 sec), and then taking the average of these values over the segment/window.

Yet another variance metric may be determined by splitting the signal spectrally into sub-bands (e.g. in its simplest form, into a low and high frequency band) and then comparing the energy (variance) between the two bands (e.g. by virtue of their ratio). The smooth, low variance signal will have most energy in the LF band, while the other signals will exhibit increased energy in the HF band.

Put another way, an example approach may comprise obtaining a frequency domain representation of the values of detected movement of the subject's arm during the first time period; and then determining a measure of variance based on the obtained frequency components. For instance a measure of variance may be calculated based on a mean or median frequency of the frequency domain representation, or by undertaking a comparison of low and high frequency bands of the frequency domain representation of the values of detected movement. Another variance measure may be based on a modal frequency of the frequency domain representation of the values of detected movement.

It has also been identified that it may be preferable to observe the subject's sensed arm movement for periods of time adjacent to the moments of leaving a location and arriving at another location. This is premised on the thought that, in these periods, it is most likely the subject was walking. Other strategies are not excluded, however. For example, sensed arm movement for complete time period between leaving a first location and arrival at a second location can be observed. Another approach may be to compute the fraction of high variance in the sensed arm movement over that complete period.

Figure 3:
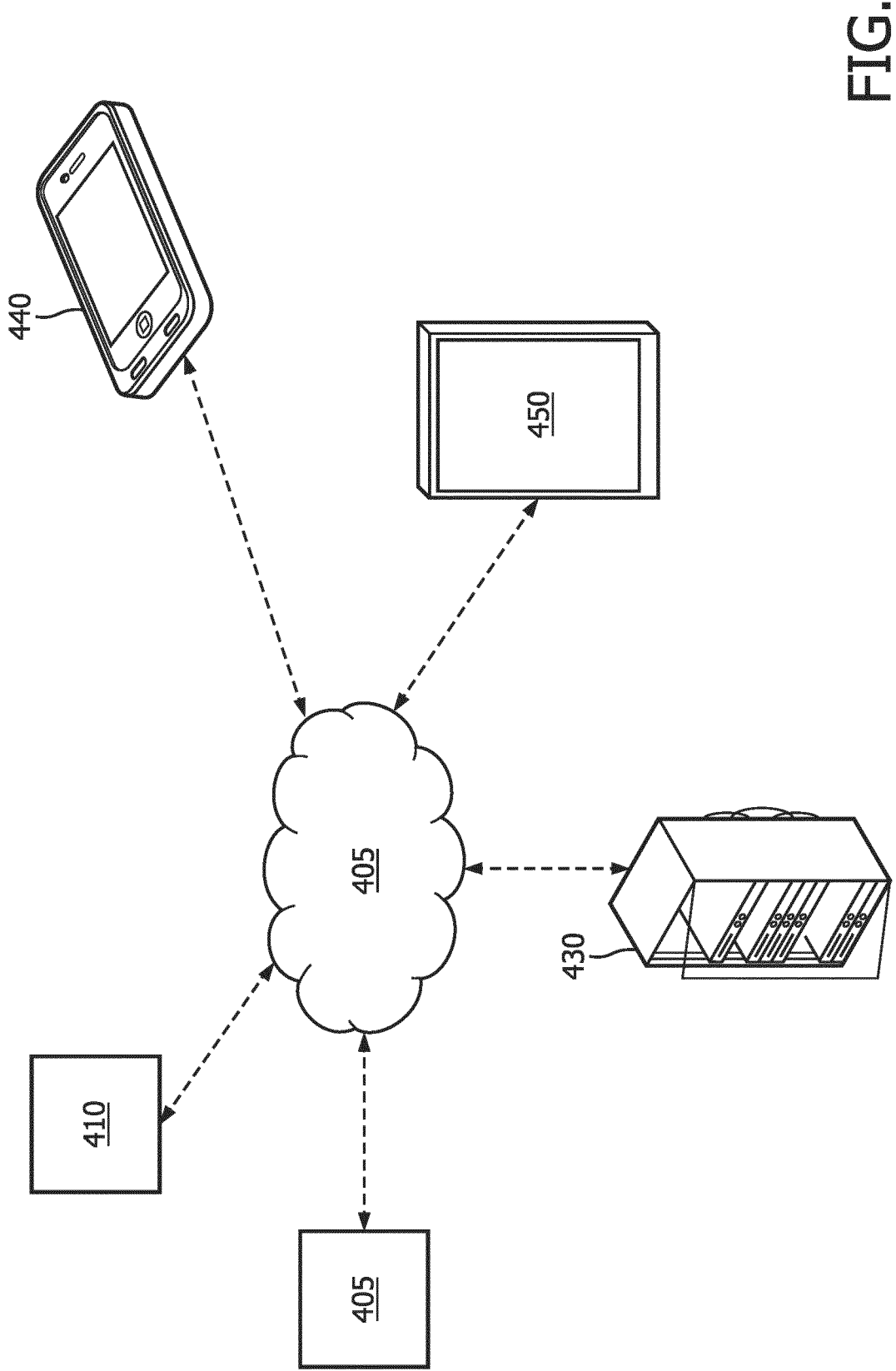
FIG. 3 is a simplified block diagram of a system for monitoring a subject according to another embodiment.

Referring now to FIG. 3, there is depicted a system comprising a sensor arrangement 405 adapted to detect movement of the subject between the first and second locations and to generate an indication of the first time period during which the subject is detected to have transferred between first and second locations. Here, the sensor arrangement 405 comprises at least one of: an accelerometer; a gyroscope; a movement sensor; a weight sensor; a pressure sensor; a passive infra-red sensor; and a wireless communication signal strength sensor, and is provided as part of a conventional subject monitoring system. It will, however, be understood that, in alternative embodiments, movement of the subject between the first and second locations may be detected using any suitable sensors strategically positioned within a monitoring environment.

The system also comprises a wrist-worn movement sensor 410. Here, the wrist-worn movement sensor 410 comprises a high-resolution tri-axis accelerometer 410 adapted to be integrated into a watch or wrist-band that is worn on a wrist of the monitored subject. The accelerometer-based movement sensor 410 is adapted to output one or more signals representative of the detected value(s) of a subject's wrist/hand movement during (at least) the first time period.

The sensor arrangement 405 and the wrist-worn movement sensor 410 each communicate the output signals via the Internet 420 (using a wired or wireless connection for example) to a remotely located data processing system 430 for monitoring walker usage by a subject (such as a server).

The data processing system 430 is adapted to receive the output signals from sensor arrangement 405 and the wrist-worn movement sensor 410.

The data processing system 430 processes the received signals in accordance with a method according to a proposed embodiment to determine walker usage of the monitored subject. More specifically, the method determines a measure of variance in the values of detected movement of the subject's wrist during a first time period (that has been detected as when the subject is transferred between first and second locations), and determines if the subject used a walker during the first time period based on the determined measure of variance.

The data processing system 430 is further adapted to generate output signals representative of a determined walker usage of the monitored subject. Thus, the data processing 430 provides a centrally accessible processing resource that can receive information from the sensor arrangement 405 and the wrist-worn movement sensor 410 and run one or more algorithms to transform the received information into a description of a walker usage by the monitored subject. Information relating to the determined walker usage can be stored by the data processing system (for example, in a database) and provided to other components of the system. Such provision of information about a detected or inferred walker usage by the monitored subject may be undertaken in response to a receiving a request (via the internet 420 for example) and/or may be undertaken without request (i.e. 'pushed').

For the purpose of receiving information about a detected or inferred walker usage from the data processing system, and thus to enable the subject's walker usage to be monitored and/or assessed, the system further comprises first 440 and second 450 mobile computing devices.

Here, the first mobile computing device 440 is a mobile telephone device (such as a smartphone) with a display for displaying graphical elements representative of a subject's walker usage. The second mobile computing device 450 is a mobile computer such as a Laptop or Tablet computer with a display for displaying graphical elements representative of a subject's walker usage.

The data processing system 430 is adapted to communicate output signals to the first 440 and second 450 mobile computing devices via the internet 420 (using a wired or wireless connection for example). As mentioned above, this may be undertaken in response to receiving a request from the first 440 or second 450 mobile computing devices.

Based on the received output signals, the first 440 and second 450 mobile computing devices are adapted to display one or more graphical elements in a display area provided by their respective display. For this purpose, the first 440 and second 450 mobile computing devices each comprise a software application for processing, decrypting and/or interpreting received output signals in order to determine how to display graphical elements. Thus, the first 440 and second 450 mobile computing devices each comprise a processing arrangement adapted to one or more values representative of the subject's walker usage, and to generate a display control signal for modifying at least one of the size, shape, position, orientation, pulsation or colour of the graphical element based on the one or more values representative of determined walker usage.

The system can therefore communicate information about an inferred or detected walker usage by monitored subject to users of the first 440 and second 450 mobile computing devices. For example, each of the first 440 and second 450 mobile computing devices may be used to display graphical elements to a medical practitioner, a caregiver, a family member or close relative.

Implementations of the system of FIG. 3 may vary between: (i) a situation where the data processing system 430 communicates output-ready data, which may for example comprise speaker data or display data including text and/or graphical elements (e.g. in JPEG or other image formats) that are simply provided to a user of a mobile computing device using conventional output interfaces; to (ii) a situation where the data processing system 430 communicates raw data set information that the receiving mobile computing device then processes to determine a measure of reliability of vital signs, and then provides output signals based on the determined change (for example, using local software running on the mobile computing device). Of course, in other implementations, the processing may be shared between the data processing system 430 and a receiving mobile computing device such that part of the data generated at data processing system 430 is sent to the mobile computing device for further processing by local dedicated software of the mobile computing device. Embodiments may therefore employ server-side processing, client-side processing, or any combination thereof.

Further, where the data processing system 430 does not 'push' information (e.g. output signals), but rather communicates information in response to receiving a request, the user of a device making such a request may be required to confirm or authenticate their identity and/or security credentials in order for the information to be communicated.

Exemplary potential applications and/or uses of proposed embodiments may be as follows:

Example 1

If certain time periods are classified as 'walking with walker', while others are classified as 'walking without walker', walking parameters like speed, balance and fall risk per situation may be compared. This will enable a user or caregiver to determine a pattern or trend in walker usage, which may, in turn, facilitate identification of when the monitored subject is in need for more mobility support, e.g. a wheelchair.

Example 2

If an embodiment determines that a subject is leaving his/her house and not using a walker, it may be adapted to generate a notification (e.g. reminder) to prompt the subject to use a walker.

Example 3

Existing smartwatches can already distinguish many activities from a movement pattern, like walking, sitting, sleeping. In the same way, walking with or without walker could be added as separate activities.

Example 4

Accuracy may be improved if the subject wears/carries a second sensor. Such an additional sensor may comprise a device in the form of a pendant, bracelet, or may even be a smartphone with an accelerometer. Data/signals from the second sensor may be used to identify a general walking pattern, and the data/signals from an arm-worn sensor may be used to determine whether or not the walker was used.

Figure 4:
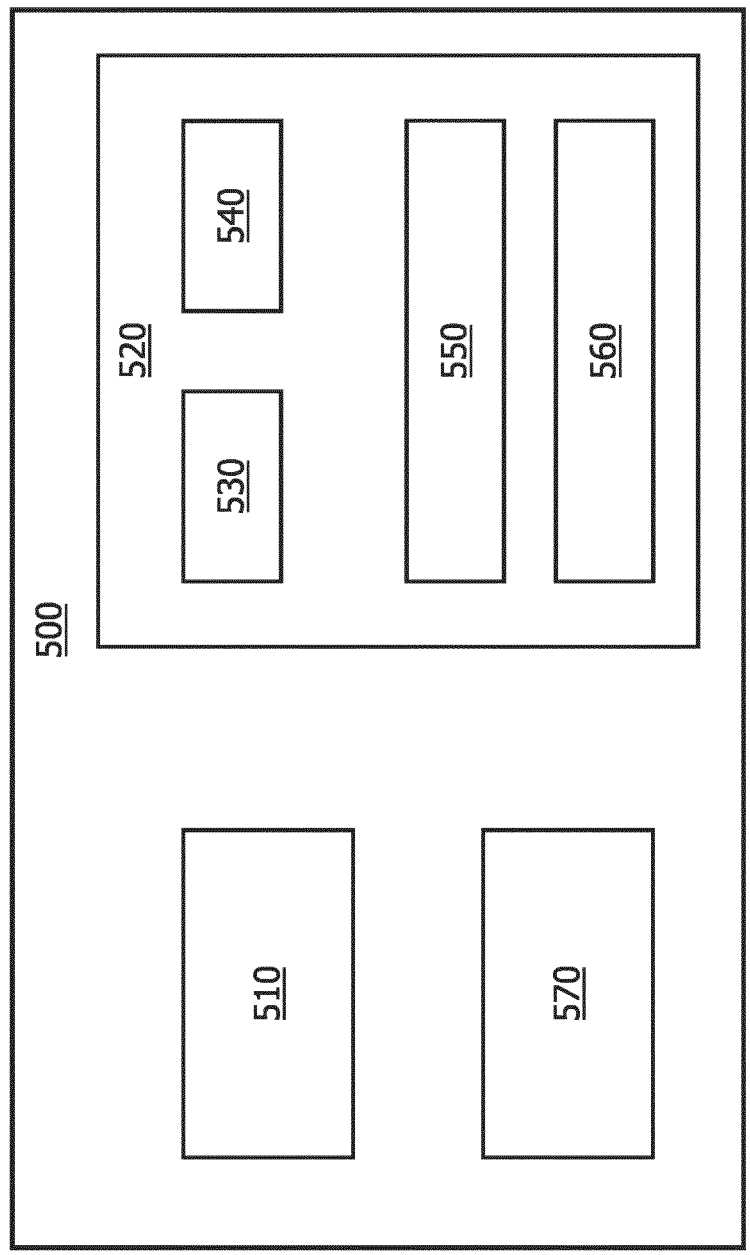
FIG. 4 is a simplified block diagram of a computer within which one or more parts of an embodiment may be employed.

FIG. 4 illustrates an example of a computer 500 within which one or more parts of an embodiment may be employed. Various operations discussed above may utilize the capabilities of the computer 500. For example, one or more parts of a monitoring system adapted to monitor a subject may be incorporated in any element, module, application, and/or component discussed herein.

The computer 500 includes, but is not limited to, PCs, workstations, laptops, PDAs, palm devices, servers, storages, and the like. Generally, in terms of hardware architecture, the computer 500 may include one or more processors 510, memory 520, and one or more I/O devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a digital signal processor (DSP), or an auxiliary processor among several processors associated with the computer 500, and the processor 510 may be a semiconductor based microprocessor (in the form of a microchip) or a microprocessor.

The memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the memory 520 may include one or more separate programs, each of which comprises an ordered listing of executable instructions for implementing logical functions. The software in the memory 520 includes a suitable operating system (O/S) 550, compiler 540, source code 530, and one or more applications 560 in accordance with exemplary embodiments. As illustrated, the application 560 comprises numerous functional components for implementing the features and operations of the exemplary embodiments. The application 560 of the computer 500 may represent various applications, computational units, logic, functional units, processes, operations, virtual entities, and/or modules in accordance with exemplary embodiments, but the application 560 is not meant to be a limitation.

The operating system 550 controls the execution of other computer programs, and provides scheduling, input-output control, file and data management, memory management, and communication control and related services. It is contemplated by the inventors that the application 560 for implementing exemplary embodiments may be applicable on all commercially available operating systems.

Application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, php. Python, ASP scripts, FORTRAN, COBOL, Perl, Java, ADA, .NET, and the like.

The I/O devices 570 may include input devices such as, for example but not limited to, a mouse, keyboard, scanner, microphone, camera, etc. Furthermore, the I/O devices 570 may also include output devices, for example but not limited to a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or intranet.

If the computer 500 is a PC, workstation, intelligent device or the like, the software in the memory 520 may further include a basic input output system (BIOS) (omitted for simplicity). The BIOS is a set of essential software routines that initialize and test hardware at startup, start the O/S 550, and support the transfer of data among the hardware devices. The BIOS is stored in some type of read-only-memory, such as ROM, PROM, EPROM, EEPROM or the like, so that the BIOS can be executed when the computer 500 is activated.

When the computer 500 is in operation, the processor 510 is configured to execute software stored within the memory 520, to communicate data to and from the memory 520, and to generally control operations of the computer 500 pursuant to the software. The application 560 and the O/S 550 are read, in whole or in part, by the processor 510, perhaps buffered within the processor 510, and then executed.

When the application 560 is implemented in software it should be noted that the application 560 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 560 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Various embodiments may include a system, a method, and/or a computer program product. The computer program product may include a computer readable storage medium (or media) having computer readable program instructions thereon for causing a processor to carry out aspects of the various embodiments described herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the various embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, optimized for embedded implementation, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the various embodiments described herein.

Aspects of the various embodiments described herein are described with reference to flowchart illustrations and/or block diagrams of methods, apparatus (systems), and computer program products according to the embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments described herein. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it will be appreciated that embodiments may therefore be useful for monitoring of elderly, disabled, rehabilitation patients, or unwell individuals so as to support independent living. Information about inferred walker usage can be used both for real-time monitoring and alerts, as well as to detect when walker usage deviates from usual or expected patterns or trends.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand that various embodiments with various modifications are contemplated.

The invention claimed is:

1. A system for monitoring walker usage by a subject, the system comprising:
an input interface adapted to obtain an indication of a first time period during which the subject is determined to have transferred between a first location and a second location;
a data acquisition unit adapted to obtain movement data comprising values of detected movement of an arm of the subject over the first time period;
a data analysis unit adapted to:
obtain a frequency domain representation of the values of detected movement of an arm of the user during the first time period and the second time period, and
determine a measure of variance in the values of detected movement of an arm of the user during the first time period and the second time period based on at least one of:
a mean or median frequency of the frequency domain representation of the values of detected movement,
a comparison of low and high frequency bands of the frequency domain representation of the values of detected movement, and
a modal frequency of the frequency domain representation of the values of detected movement; and
a monitor unit adapted to determine if the subject used a walker during the first time period while transferring from the first location to the second location based on the determined measure of variance over the first time period and to classify at least one time subperiod of the first period as "walking with walker" and at least one other time subperiod of the first time period as "walking without walker".

2. The system of claim 1, wherein the monitor unit is adapted:
to compare the determined measure of variance with a threshold value; and
to determine the subject has not used a walker during the first time period if the determined measure of variance exceeds the threshold value.

3. The system of claim 2, wherein the monitor unit is adapted to determine the threshold value based on at least one of: a user input provided to the system; a predetermined value; and a physiological property of the subject.

4. The system of claim 3, wherein the monitor unit is adapted to determine the threshold value based on a value of the physiological property of the subject, and wherein the physiological property comprises height, weight, age, gender or level of fitness.

5. The system of claim 1, further comprising:
a sensor arrangement adapted to detect movement of the subject between the first and second locations and to generate an indication of the first time period during which the subject is detected to have transferred between first and second locations.

6. The system of claim 5, wherein the sensor arrangement comprises at least one of: an accelerometer; a gyroscope; a movement sensor; a weight sensor; a pressure sensor; a passive infra-red sensor; and a wireless communication signal strength sensor.

7. The system of claim 1, further comprising a movement sensor adapted to be worn on an arm of the subject and to generate movement data comprising values of detected movement of an arm of the subject.

8. The system of claim 7, wherein the movement sensor is adapted to be worn on a forearm, wrist or hand of the subject.

9. The system of claim 1, wherein the data analysis unit is adapted to determine a measure of variance in the values of detected movement of an arm of the subject during the first time period based on at least one of: an average value of the values of detected movement; a median value of the values of detected movement; maximum and minimum values of the values of detected movement; a median of absolute deviations from the median value of the values of detected movement; a value of standard deviation of the values of detected movement.

10. A method for monitoring walker usage by a subject, the method comprising:
  obtaining an indication of a first time period during which the subject is determined to have transferred between first and second locations;
  obtaining movement data comprising values of detected movement of an arm of the subject during the first time period;
  determining a measure of variance in the values of detected movement of an arm of the subject during the first time period based on at least one of:
    a mean or median frequency of the frequency domain representation of the values of detected movement,
    a comparison of low and high frequency bands of the frequency domain representation of the values of detected movement, and
    a modal frequency of the frequency domain representation of the values of detected movement;
  determining if the subject used a walker during the first time period while transferring from the first location to the second location based on the determined measure of variance over the first time period; and
  classifying at least one time subperiod of the first period as "walking with walker" and at least one other time subperiod of the first time period as "walking without walker".

11. The method of claim 10, wherein determining if the subject used a walker comprises:
  comparing the determined measure of variance with a threshold value; and
  determining the subject has not used a walker during the first time period if the determined measure of variance exceeds the threshold value.

12. The method of claim 11, further comprising determining the threshold value based on at least one of: a user input provided to the system; a predetermined value; and the subject.

13. The method of claim 10, further comprising:
  detecting movement of the subject between the first and second locations; and
  generating an indication of the first time period during which the subject is detected to have transferred between first and second locations.

14. A non-transitory computer-readable storage medium comprising computer readable code storable on, or stored on, or downloadable from a communications network, which code when run on a computer implements the method of claim 10.

* * * * *